Figure 1:
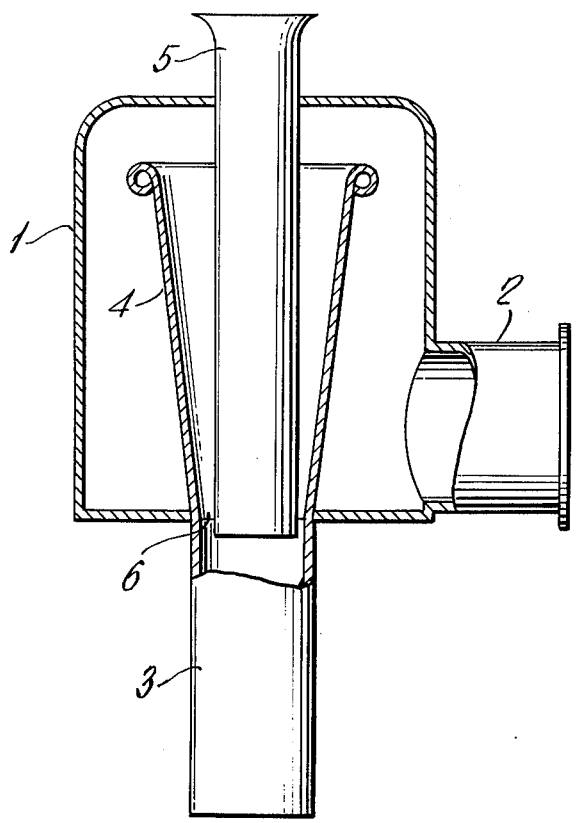

United States Patent [19]

Liepe et al.

[11] 3,960,175

[45] June 1, 1976

[54] INSTALLATION FOR CHARGING LIQUIDS, PARTICULARLY FERMENTATION LIQUIDS, WITH GAS

[75] Inventors: Friedrich Liepe; Gerhard Langhans, both of Dresden; Leonhard Jagusch, Leipzig; Klaus Richter; Güenter Schlaf, both of Dresden, all of Germany

[73] Assignee: VEB Chemieanlagenbau und Montagekombinat Leipzig, Leipzig, Germany

[22] Filed: Aug. 16, 1974

[21] Appl. No.: 497,974

[52] U.S. Cl.............................. 137/604; 261/DIG. 75; 417/183
[51] Int. Cl.² ........................................ F16K 19/00
[58] Field of Search ....... 137/604; 261/76, DIG. 62, 261/DIG. 75; 417/183

[56] References Cited
UNITED STATES PATENTS

| 487,887 | /1892 | Howell | 261/DIG. 75 |
| 894,758 | 7/1908 | Starre | 417/197 |
| 2,328,414 | 8/1943 | Beyer | 261/DIG. 75 |

Primary Examiner—Robert G. Nilson
Attorney, Agent, or Firm—Nolte and Nolte

[57] ABSTRACT

Apparatus for charging a liquid with a gas comprising a container with a liquid inlet port toward the bottom thereof, a gas inlet extending through an upper wall of the container towards a jet pipe in the lower wall and an insert extending upwardly from the top of the jet pipe and around the air inlet pipe, the insert being generally conical and tapering towards its union with the jet pipe.

9 Claims, 4 Drawing Figures

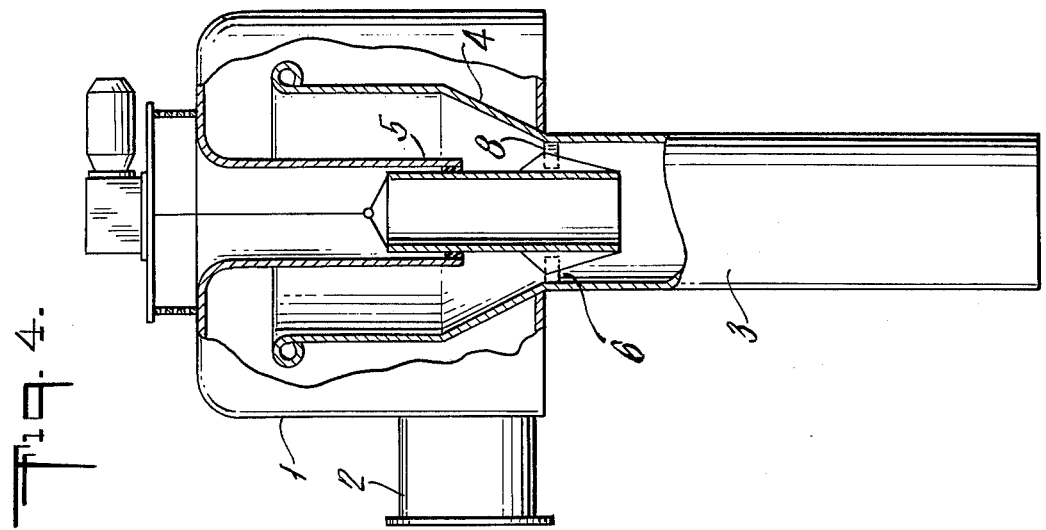
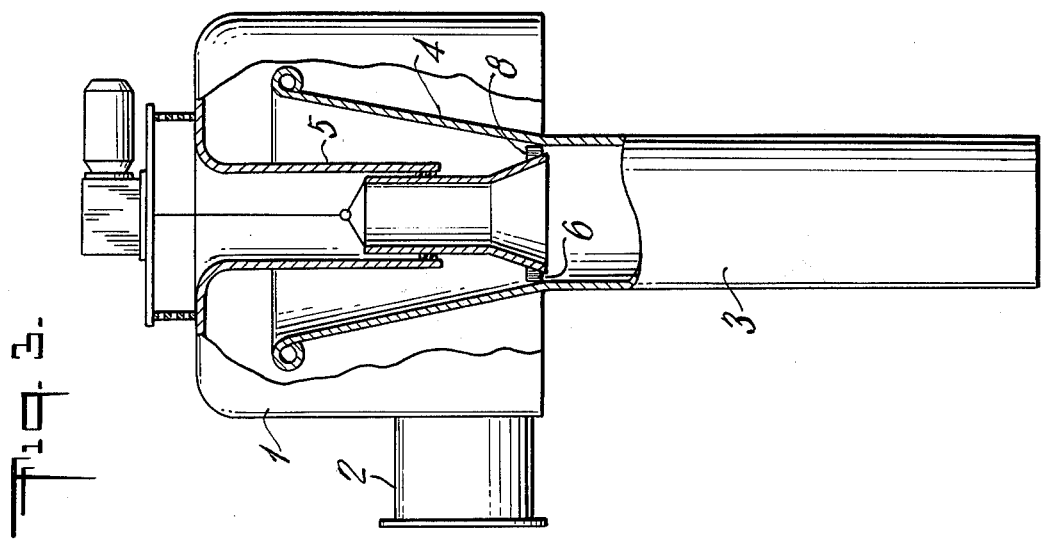

INSTALLATION FOR CHARGING LIQUIDS, PARTICULARLY FERMENTATION LIQUIDS, WITH GAS

The invention concerns a pressure jet, which is equipped with a liquid- and an air-inlet connection, for charging liquids, particularly fermentation liquids and waste water, with gas.

A Venturi tube mixer for making gas dispersions is known, in the housing of which the profiled parts forming a gap are arranged in such a manner that the one profiled part is fixed, while the other profiled part can be adjusted, for instance, by means of a spindle equipped with a hand wheel. At its apex, the fixed profiled part is provided with toothlike notches. Underneath these notches, a hole runs through the fixed profiled body, through which gas is fed in. The liquid flowing through the Venturi tube mixer causes the gas to be taken along.

Jets are furthermore known which operate according to the injection principle.

Both types of device have the disadvantage that the gas is fed in and dispersed at that point where the velocity is very high as compared to the velocity of the two-phase system flowing out of the device. This causes a considerable reduction of the pressure at the gas dispersion point. For this reason, the ratio of the momentum of the two-phase mixture to the power supplied is unfavorable, and furthermore, the pressure drop causes a large increase of the local gas component, which promotes coalescence.

It is the purpose of the invention to create a pressure jet, which achieves good dispersion of the gas in the liquid with little expenditure of energy.

It is an object of the invention to develop a pressure jet which is of such design that formation of the mixture and the gas dispersion take place at separate points, it being assured that the gas-liquid mixture leaves the pressure jet with a large momentum.

According to the invention, the problem is solved by the provision that the pressure jet consists of a cylindrical or conical vessel, at the lower part of which the liquid inlet connection is arranged and at whose bottom a jet pipe is arranged approximately vertically, whose diameter is smaller than the diameter of the vessel and which is provided at at its upper end with a conical insert extending into the vessel. The lower diameter of the insert corresponds to the diameter of the jet pipe. In the insert a vertically disposed gas inlet pipe, leading to the outside, is provided, whose lower end, together with the jet pipe, forms a ring gas which increases the velocity of the liquid. The ratio of the cross sections of the ring gap and the gas inlet pipe is made here like that of the volume flow of the liquid and the gas.

In an improvement of the invention, the lower end of the gas inlet pipe is made pleated. The gas inlet pipe can also be subdivided by partitions into individual sectors, where the sectors have separate gas inlet connections.

The lower end of the jet pipe can also be designed as a nozzle. A further variant provides that the jet pipe is made conical, having its smallest diameter at the lower end. It is advisable to round off the upper edge of the insert.

In a further embodiment of the pressure jet, the gas inlet pipe or the lower part thereof is movable in the vertical direction. The lower part of the gas inlet pipe is conically enlarged and is provided at its outer circumference with several elements to break up the flow. Another variant provides that the lower part of the gas inlet pipe is enlarged, several flow-breakup elements being arranged at the upper end of the jet pipe. The flow-breakup elements have a gas passage opening, which connects with a respective gas inlet opening in the jet pipe.

In the pressure jet according to the invention the gas dispersion and the formation of the mixture of the gas and the liquid take place at separate points. The mixture is formed at a pressure which is lower by at most only 100 mm water column than the system pressure. Because the velocity of the gas and the liquid is the same, the pressure loss in the formation of the mixture is minimal. The dispersion takes place at the jet pipe exit or upon the entrance of the liquid-gas mixture into the liquid of the vessel located under the pressure jet. Here exists the possibility of distributing the bubbles in the radial direction by the turbulent diffusion. In addition, a large momentum or power charge at the jet pipe exit is produced during the formation of the mixture due to the small pressure loss.

Figure 2:
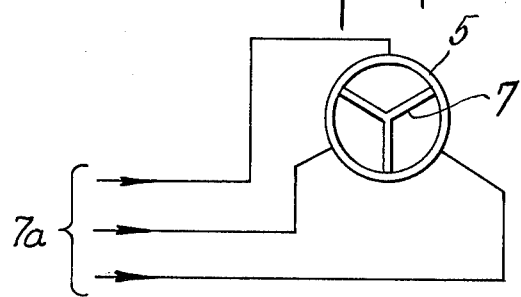

The invention will be explained in further detail in the following with the aid of an example of an embodiment. There is shown in FIG. 1, a longitudinal cross section through the pressure jet, FIG. 2, a top view onto the gas inlet pipe, FIG. 3, a longitudinal cross section through the pressure jet with a conical enlargement of the gas inlet pipe, and in FIG. 4, a longitudinal cross section through the pressure jet with another enlargement of the gas inlet pipe.

The pressure jet consists of the closed vessel 1, whose diameter is 1300 mm. At the lower part of the vertically disposed vessel 1, the liquid inlet connection 2 is provided. Its diameter is 800 mm. The 1.5-meter long jet pipe 3 is vertically arranged at the bottom of the vessel 1. It has a diameter of 400 mm. At the bottom of the vessel 1 is attached in the interior an insert 4, which expands conically toward the top. The lower diameter of this insert corresponds to the diameter of the jet pipe 3. The lower end of the insert 4 is connected with the upper end of the jet pipe 3. In order to ensure better flow for the liquid in the vessel 1, the upper end of the insert 4 is rounded off. In the insert 4 a vertically disposed gas inlet pipe 5, leading to the outside, is provided, whose lower end, together with the jet pipe 3, forms a ring gap 6, which increases the velocity of the liquid. The gas inlet pipe 5 has a diameter of 280 mm. Its lower end is advantageously located at the height of the upper end of the jet pipe 3. However, it can also extend somewhat into the jet pipe 3. In order to make charging with different gases possible, the gas inlet pipe 5 is subdivided into several sectors by means of partitions 7 and separate gas inlet lines 7a, shown schematically in FIG. 2, lead to respective ones of the sectors. This is advantageous particularly in cases where gases are mixed with the liquid, with together form an explosive mixture. The size of the diameter of the gas inlet pipe 5 depends particularly on the ratio of the amount of liquid fed-in to the amount of gas fed-in that is to be achieved. With the dimensions given, the cross section area of the gas inlet pipe 5 is 630 cm$^2$ and that of the ring 6 likewise 630 cm$^2$. As the gas inlet pipe 5 as well as also the ring gap 6 have the same cross section area, the volume of the liquid fed-in and the volume of the gas fed-in have the ratio 1:1. The ratio can be varied so, however, that four times more gas volume is drawn in than liquid volume.

In order to achieve a better mixture formation and to reduce the slippage between the liquid and the gas, the lower end of the gas inlet pipe 5 is made pleated. It is, moreover, possible to design the lower end of the jet pipe 3 as a nozzle.

The liquid, which is at an overpressure of 1.2 atm arrives in the vessel 1 through the liquid inlet connection 2. Its velocity is here up to 2.5 m/s. ensured liquid rises in the vessel 1 and then gets into the insert 4, in which the velocity increases continuously. At the upper end of the jet pipe 3 it is 12 to 16 m/s. At the lower end of the gas inlet pipe 5 or the upper end of the jet pipe 3, the formation of the gas-liquid mixture takes place. As at this point the liquid as well as the gas have the same velocity, the pressure loss during the formation of the mixture is extremely minimal. The gas-liquid mixture practically retains its velocity as it flows through the jet pipe 3. Thus, it still has the velocity of 12 to 16 m/s at the lower end of the jet pipe. In this manner it becomes possible that the gas-liquid mixture enters the liquid of the vessel located underneath the pressure jet with a large momentum or velocity and intensive dispersion is obtained there.

In a pressure jet according to FIG. 3, the gas inlet pipe 5 or the lower part thereof can be moved in the vertical direction. This movability and the possibility of locking is ensuring by known mechanical means, e.g., via a lead screw or a piston rod (similar to a pump handle). By moving the gas inlet pipe 5, a change of the flow cross section occupied by the liquid (ring gap 6) is achieved. Thus, moving the gas inlet pipe 5 upward causes an increase of the ring gap 6, whereby the flow velocity of the liquid in the ring gap 6 and in the opening of the jet pipe 3 is decreased. Thereby, also the power charge (flow momentum) and the amount of gas taken along are changed. Through this control possibility, adaption to different operating conditions is obtained.

It has been found practical to enlarge the lower end of the gas inlet pipe 5 conically, so that it has a larger diameter than its upper part. In addition, the lower end of the gas inlet pipe 5 is provided with 6 to 8 flow-breakup elements 8, which break up the liquid flow in the ring gap 6.

In another variant according to FIG. 4, the outside diameter of the lower part of the gas inlet pipe 5 is enlarged so that the largest outside diameter is provided not at the lower end of the gas inlet pipe 5, but at a distance above it, the outside diameter of the lower end corresponding to the outside diameter of the upper part of the gas inlet pipe 5. Here, the gas inlet pipe 5 extends into the upper part of the jet pipe 3. The flow-breakup elements 8 are arranged at the inside wall of the upper end of the jet pipe 3. When the lower part of the gas inlet pipe 5 is moved, the flow-breakup elements 8 slide in corresponding slots, which are arranged in the enlargement of the lower part of the gas in let pipe 5. In order to assure reliable separation of the liquid flow from the outside wall of the gas inlet pipe 5 in the ring gap 6, in the flow plane in which the flow-breakup elements 8 are disposed, the liquid flow is vented behind the flow-breakup elements 8. Similarly, the breaking up of the liquid flow behind the flow-breakup elements, as seen in the flow direction of the liquid, is ensured by the venting. For this purpose the flow-breakup elements 8 are made hollow and have holes or slots on the backside of the flow, to permit the passage of gas. At the point of their attachment at the upper end of the jet pipe 3, gas inlet openings are provided in the latter. The gas that has entered, after passing the flow-breakup elements 8, gets through these gas inlet openings into the liquid flowing through the ring gap 6 and vents the former additionally. In case the flow-breakup elements 8 are not made hollow, the venting is accomplished by gas inlet openings which are arranged in the jet pipe 3 below the flow-breakup elements 8, where the gas that has arrived in the jet pipe 3 can get directly into the liquid that flows through the ring gap 6. The gas entering the gas inlet openings is either drawn in from the environment of the pressure jet or fed-in from another place via a separate pipe line, preferably via a ring line adjacent to the jet pipe 3. In this manner, the liquid flowing through the pressure jet is mixed with gas, which is fed in via the gas inlet pipe 5 as well as through the gas inlet openings in the jet pipe 3.

The design of the pressure jet also makes it possible to introduce a gas-liquid mixture into the vessel 1 through the liquid inlet connection 2. This possibility is utilized particularly if several different gases are fed to the pressure jet, which together form an explosive mixture and if highly emulsifying liquids are charged with gas, in which the liquid still contains considerable gas components also behind the pump. In case one liquid inlet connection 2 cannot handle all the liquid, several such liquid inlet connections 2 are arranged at the vessel 1.

We claim:

1. Pressure jet apparatus for charging a liquid with gas comprising a generally circular sectioned vessel disposed with its axis substantially vertical and having a top and bottom wall, a liquid inlet connection opening to said vessel adjacent the bottom wall thereof, a generally circular sectioned jet pipe leading downwardly from the bottom of the vessel for conducting liquid charged with gas from the vessel, an upwardly diverging, generally vertically disposed, conical insert secured to the upper end of said jet pipe and extending upwardly toward the top wall of said vessel, the lower end of said insert being of similar diameter to that of the upper end of said jet pipe, a vertically disposed gas inlet pipe arranged concentrically with said jet pipe and extending through the top wall and terminating close to the upper end of said jet pipe and defining there with an annular gap, that gap constituting means accelerating liquid passing therethrough, said jet pipe being free of diverging portions and the ratio of the cross sectional areas of said gas inlet pipe and said gap being directly related to the ratio of flows of gas and liquid through said pipe and said gap respectively.

2. Pressure jet apparatus as claimed in claim 1 wherein longitudinal partition means are provided in the gas inlet pipe and are effective to divide said gas inlet pipe into individual sectors each said sector having a separate gas inlet connection.

3. Pressure jet apparatus according to claim 1 wherein the lower end of the jet pipe is designed as a nozzle.

4. Pressure jet apparatus according to claim 1 wherein a lower portion of the jet pipe is conical, having its lesser diameter at the lower end thereof.

5. Pressure jet apparatus according to claim 1 wherein the upper edge of the insert is rounded off.

6. Pressure jet apparatus according to claim 1 wherein at least the lowermost portion of the gas inlet pipe is movable in the vertical direction to constitute means varying the cross sectional area of said gap.

7. Pressure jet apparatus according to claim 1 wherein a lowermost portion of said gas inlet pipe is conical, having its greater diameter lowermost and wherein said portion is provided at its outer circumference with several flow-breakup elements.

8. Pressure jet apparatus according to claim 1 wherein a lowermost part of the gas inlet pipe has an enlargement and wherein several flow-breakup elements are arranged at the upper end of the jet pipe.

9. Pressure jet apparatus as claimed in claim 8 wherein said flow-breakup elements have a gas passage opening which connects with the respective gas inlet openings in the jet pipe.

* * * * *